US005670676A

United States Patent [19]
Draper et al.

[11] Patent Number: 5,670,676
[45] Date of Patent: *Sep. 23, 1997

[54] PROCESS FOR PREPARATION OF 9α-CHLORO-11β FORMYLOXYPREGNA-3.20-DIONES

[75] Inventors: Richard W. Draper, North Caldwell; Eugene J. Vater, Lyndhurst, both of N.J.

[73] Assignee: Schering Corporation, Kenilworth, N.J.

[*] Notice: The term of this patent shall not extend beyond the expiration date of Pat. No. 5,602,248.

[21] Appl. No.: 455,967

[22] Filed: May 31, 1995

Related U.S. Application Data

[63] Continuation of Ser. No. 405,472, Mar. 16, 1995, abandoned.

[51] Int. Cl.$^6$ .................... C07J 5/00; C07J 7/00; C07J 43/00; C07J 33/00
[52] U.S. Cl. ................. 552/574; 540/61; 540/63; 540/69; 540/70; 540/114; 540/115; 540/116; 540/118; 540/119; 552/564; 552/565; 552/566; 552/567; 552/568; 552/570; 552/571; 552/576; 552/577; 552/579
[58] Field of Search ................ 540/61, 63, 69, 540/70, 114, 115, 116, 118, 119; 552/564, 565, 566, 567, 568, 570, 571, 574, 576, 577, 579

[56] References Cited

U.S. PATENT DOCUMENTS 4,525,303   6/1985   Takagaki et al. ............... 260/239.55

OTHER PUBLICATIONS

Translation of East German DD 268 954 A1 (1989).

*Primary Examiner*—Kimberly J. Prior
*Attorney, Agent, or Firm*—Henry C. Jeanette

[57] ABSTRACT

Disclosed is a process for producing a compound of the formula:

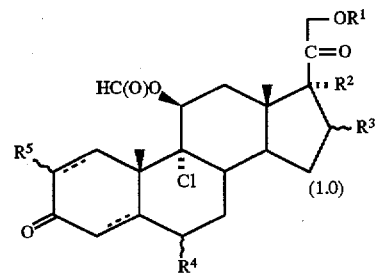

by reacting a compound of the formula:

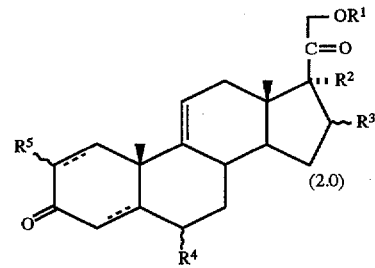

with: (1) a chlorinating reagent selected from an N-chloroimide or an N-chloroamide; (2) an anhydrous strong acid selected from orthophosphoric acid, alkylsulfonic acids, fluoroalkylsulfonic acids or arylsulfonic acids; and (3) anhydrous dimethylformamide; at a temperature within the range of about −78° to about 0° C.

22 Claims, No Drawings

1

PROCESS FOR PREPARATION OF 9α-CHLORO-11β FORMYLOXYPREGNA-3,20-DIONES

CROSS REFERENCE TO RELATED APPLICATION

This is a continuation of application Ser. No. 08/405,472 filed Mar. 16, 1995 now abandoned.

BACKGROUND

A translation of East German 268954 A1 discloses a process for preparing steroids of the pregnane series which contain a 9α-halogen-11α-formyloxy group. Steroids with these substituents are precursors to the respective 9α-halo, 11β-hydroxysteroids. In view of the importance of 9α-halo, 11β-hydroxysteroids, processes which produce their precursors in high yield with a minimum of by-products would be a welcome contribution to the art. The claimed invention provides just such a contribution.

SUMMARY OF THE INVENTION

The claimed invention is directed to a process for producing 9α-chloro-11β-formyloxypregna-3,20-diones from their 9,11 double bond precursors. The use of a strong acid, anhydrous reaction conditions and low reaction temperatures produces a 9α-chloro-11β-formyloxypregna-3,20-dione with minimal formation of the 9α, 11β-dichloro or 9α-chloro-11β-hydroxy by-products.

The claimed invention is directed to a process for producing a compound of the formula:

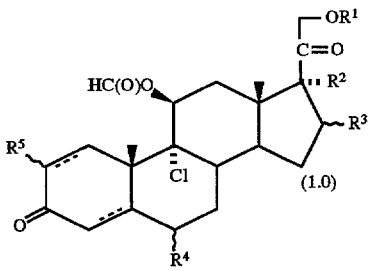

wherein:
the broken lines represent optional bonds;
$R^1$ represents an acyl radical of: (1) a hydrocarbon carboxylic acid having from 2 to 12 carbon atoms; or (2) benzoic acid substituted by a halogen or methoxy group;
$R^2$ is selected from hydroxy or —$OR^6$;
$R^3$ is selected from hydrogen, lower alkyl or α—$OR^7$; or $R^2$ and $R^3$ taken together represent a 16α, 17α-lower alkylidenedioxy having up to 13 carbon atoms;
$R^4$ is selected from hydrogen, α-methyl, α-bromo, α-chloro, α-fluoro, β-fluoro and α-fluoromethyl;
$R^5$ is selected from hydrogen, methyl, fluorine, chlorine and bromine;
$R^6$ is an acyl radical of: (1) a hydrocarbon carboxylic acid having from 2 to 12 carbon atoms (e.g., an alkyl carboxylic acid such as an alkanoic acid); (2) an aromatic carboxylic acid; (3) an arylhydrocarbon carboxylic acid; (4) a heteroaromatic carboxylic acid having at least one oxygen atom in the heteroaryl ring and wherein oxygen is the only heteroatom in the heteroaryl ring (e.g., there are no sulfur or nitrogen atoms in the heteroaryl ring); or (5) a heteroarylhydrocarbon carboxylic acid having at least one oxygen atom in the heteroaryl ring and wherein oxygen is the only heteroatom in the heteroaryl ring (e.g., there are no sulfur or nitrogen atoms in the heteroaryl ring); said acyl radical having 2 to 12 carbon atoms; and
$R^7$ is an acyl radical of a hydrocarbon carboxylic acid having from 2 to 12 carbon atoms;
said process comprising reacting a compound of the formula:

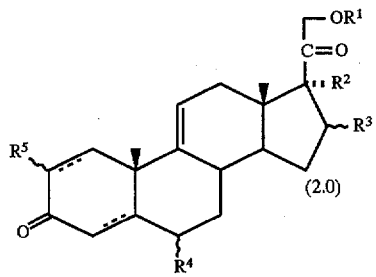

wherein $R^1$, $R^2$, $R^3$, $R^4$, and $R^5$ are as defined above, with: (1) a chlorinating reagent selected from an N-chloroimide or an N-chloroamide; (2) an anhydrous strong acid selected from orthophosphoric acid, alkylsulfonic acids, fluoroalkylsulfonic acids or arylsulfonic acids; and (3) anhydrous dimethylformamide; said reaction being conducted at a temperature within the range of about −78° to about 0° C.; said reaction being conducted under anhydrous conditions; and said reaction being conducted under an inert atmosphere.

DETAILED DESCRIPTION OF THE INVENTION

The terms below, as used herein, have the stated meaning unless otherwise defined herein:
acyl—represents a radical formed from a carboxylic acid, e.g.,

wherein $R^A$ represents a saturated hydrocarbon group (e.g., alkyl or cycloalkyl), aryl group, heteroaryl group (wherein the heteroatom or heteroatoms are oxygen), an arylhydrocarbon group or a heteroarylhydrocarbon group (wherein the heteroatom or heteroatoms are oxygen), said acyl group having up to about 12 carbon atoms (e.g., 2 to 12 carbon atoms);
alkyl- represents straight and branched carbon chains and contains from one to twenty carbon atoms, preferably one to six carbon atoms;
anhydrous—means free to substantially free of water;
aromatic (aryl)—represents a carbocyclic group containing from 6 to 12 carbon atoms and having at least one aromatic ring (e.g., aryl is a phenyl ring), with all available substitutable carbon atoms of the carbocyclic group being intended as possible points of attachment, said carbocyclic group being optionally substituted (e.g., 1 to 3) with one or more of halo, alkyl, alkoxy, phenoxy, $CF_3$, or —$NO_2$;
aromatic (aryl) carboxylic acid—represents an aromatic group as defined above having at least one —COOH group, and preferably one —COOH group;
cycloalkyl—represents a saturated carbocyclic ring having from 3 to 8 carbon atoms;

DMF—represents dimethylformamide;

heteroaromatic (heteroaryl)—represents cyclic groups having at least one O atom (i.e., the only heteroatoms are oxygen), and preferably one oxygen atom, interrupting a carbocyclic ring structure and having a sufficient number of delocalized pi electrons to provide aromatic character, with the aromatic heterocyclic groups preferably containing from 2 to 14 carbon atoms, e.g., 2- or 3-furyl; or 2-, 3-, 4-, 5-, 6- or 7-benzofuranyl. Preferred heteroaryl groups are 2- or 3-furyl;

heteroaromatic (heteroaryl) carboxylic acid—represents one of the above defined heteroaryl groups with at least one —COOH group, and preferably one —COOH group;

halogen (halo)—represents Cl, F, Br and I;

hydrocarbon carboxylic acid—represents a straight or branched chain carboxylic acid having from 2 to 12 carbon atoms;

lower alkylidenedioxy—represents an alkylidene group having two oxygen atoms located on two different carbon atoms such that each oxygen atom can form a bond to a different carbon atom on the steroid ring; the alkylidenedioxy group can be generally represented as:

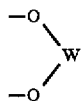

wherein W represents $(CR^B R^C)_n$; $R^B$ and $R^C$ independently represent H, alkyl, and aryl; and n represents 1 to 4 (preferably 1 or 2) such that the total number of carbon atoms in the alkylideneoxy group is no more than about 13 (e.g., 1 to 13); and lower alkyl—straight or branched chain alkyl groups having from 1 to 6 carbon atoms, e.g., methyl, ethyl, n-propyl, isopropyl, n-butyl, sec-butyl, n-pentyl, isopentyl, n-hexyl, and 2,3-dimethylbutyl.

The claimed process is carried out under anhydrous conditions and under an inert atmosphere, e.g., nitrogen.

The starting reactant of Formula 2.0 is readily available in the art. A compound of Formula 2.0 is dissolved in anhydrous DMF under an inert atmosphere, e.g., under nitrogen. A sufficient amount of DMF and compound of Formula 2.0 is used to provide the desired amount of 9α-chloro-11β-formyloxypregna-3,20-dione product of Formula 1.0. Usually, about a 0.05 to about a 3 molar solution is made, with about a 0.15 to about a 0.5 molar solution being preferred. Most preferred is about a 0.33 molar solution of the compound of Formula 2.0 in anhydrous DMF.

Preferably, the molar solution is first cooled to about 0° C., then the anhydrous strong acid is added, and then the resulting solution is further cooled to the desired reaction temperature. The reaction is usually carried out at a low temperature, usually about −78° to about 0° C., with about −55° to about −20° C. being preferred, and about −50° C. being most preferred. About 0.9 to about 2.0 equivalents of the anhydrous strong acid is added, with about 1 equivalent being preferred. Suitable anhydrous strong acids include orthophosphoric acid, alkylsulfonic acids, fluoroalkylsulfonic acids or arylsulfonic acids. Examples of anhydrous alkylsulfonic acids include: methanesulfonic acid, butanesulfonic acid, and camphorsulfonic acid, with methanesulfonic acid being preferred. Examples of anhydrous fluroroalkylsulfonic acids include: trifluoromethanesulfonic acid and perfluorobutanesulfonic acid. Examples of anhydrous arylsulfonic acids include: p-toluenesulfonic acid (p-TSA) and benzenesulfonic acid, with p-toluenesulfonic acid being preferred. Preferably, an alkylsulfonic acid is used and most preferably methanesulfonic acid is used.

A sufficient amount of chlorinating reagent is used to provide the desired amount of 9α-chloro-11β-formyloxypregna-3,20-dione product of Formula 1.0. The chlorinating reagent is generally used in an amount of about 0.8 to about 2.0 equivalents, with about 1 to about 1.05 equivalents being preferred. The chlorinating reagent is added to the mixture of starting reactant, DMF and strong acid. The chlorinating reagent is added over a time period sufficient to maintain the desired reaction temperature. Generally, the chlorinating reagent is added over a time period of about 0.1 to about 1.0 hours. Typically, the chlorinating reagent is added over a time period of about 20 minutes. The chlorinating reagent is an N-chloroimide or an N-chloroamide. Examples of chlorinating reagents include: N-chloroacetamide, N-chlorosuccinimide, 1,3-dichloro-5,5-dimethyhydantoin, or 1,3,5-trichloroisocyanuric acid. Preferably, 1,3-dichloro-5,5-dimethyhydantoin or 1,3,5-trichloroiso-cyanuric acid is used. Most preferably, 1,3,5-trichloroisocyanuric acid, i.e.,

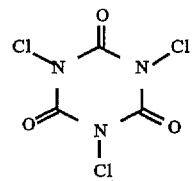

is used.

The reaction mixture (starting reactant of Formula 2.0, DMF, strong acid and chlorinating reagent) is stirred at the desired reaction temperature for a time period sufficient to result in the consumption of the starting reactant. Generally, the reaction mixture is stirred, i.e., the reaction takes place, over a time period of about 1 to about 48 hours, with about 16 to about 40 hours being preferred, and about 20 to about 30 hours being most preferred.

Preferably, a compound of Formula 1.1:

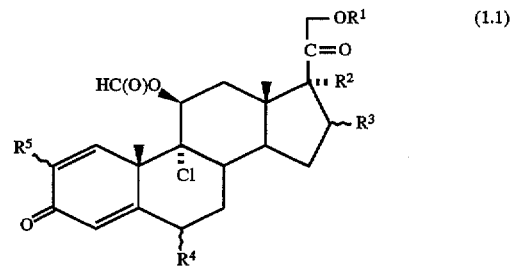

instead of Formula 1.0 is formed in the claimed process when a compound of Formula 2.1:

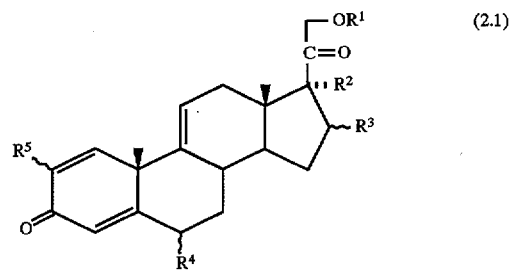

is used as the starting reactant instead of Formula 2.0.

The final product, i.e., a compound of Formula 1.0 or 1.1, if desired, can be separated from the reaction mixture and purified by techniques well known to those skilled in the art. For example, a sufficient amount of deionized water or 10% aqueous sodium sulfite is added to the reaction mixture to cause precipitation of the final product. Typically, the final product is then filtered off, washed with water and dried. Alternatively, after adding the deionized water or sodium sulfite solution, the product can be extracted into a suitable organic solvent (such as, for example, methylene chloride or ethyl acetate), washed with water and concentrated to recover the final steroid product of Formula 1.0 or 1.1. The final product can optionally be purified by crystallization or chromatography following procedures well known in the art.

$R^1$ preferably represents an acyl radical of a hydrocarbon carboxylic acid having 2 to 12 carbon atoms. Most preferably, $R^1$ represents the acyl radical of propionic acid, i.e.,

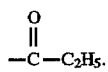

$R^2$ is preferably hydroxy (—OH) or —$OR^6$ wherein $R^6$ is an acyl radical of a hydrocarbon, aromatic or heteroaromatic carboxylic acid having 2 to 12 carbon atoms.

$R^2$ is most preferably —OH or —$OR^6$ wherein $R^6$ is the acyl radical of a hydrocarbon carboxylic acid. Hydrocarbon carboxylic acids include the alkanoic acids exemplified by acetic, propionic, trimethylacetic, butyric, isobutyric, valeric, isovaleric, caproic, tert-butylacetic, enanthic, caprylic, cyclopentylpropionic, and adamantanecarboxylic acids. Hydrocarbon carboxylic acids also include the substituted alkanoic acids such as phenoxyacetic, and β-chloropropionic acids.

Even more preferably, $R^2$ is —OH or —$OR^6$ wherein $R^6$ is is the acyl radical of propionic acid, i.e., —(O)CC$_2$H$_5$, such that $R^2$ represents

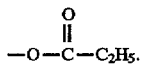

$R^2$, as stated above, can be —$OR^6$ wherein $R^6$ is an acyl radical of a heteroaromatic carboxylic acid. Examples of heteroaromatic carboxylic acids include: 2-furancarboxylic acid; 3-furancarboxylic acid; 5-bromo-2-furancarboxylic acid; 2-benzofurancarboxylic acid; and 3-benzofurancarboxylic acid. The preferred heteroaromatic carboxylic acid is 2-furancarboxylic acid. Thus, R2 can be —$OR^6$ wherein $R^6$ is the acyl radical of 2-furancarboxylic acid, i.e., $R^6$ is

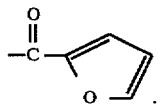

$R^6$ can also be the acyl radical of an aromatic carboxylic acid. Examples of aromatic carboxylic acids include: benzoic, toluic, p-chlorobenzoic, p-fluorobenzoic, p-methoxybenzoic, and 3', 5'-dimethylbenzoic acids.

Arylhydrocarbon carboxylic acids for $R^6$ refers to hydrocarbon carboxylic acids substituted with an aryl group (e.g., arylalkanoic acids). Examples of arylhydrocarbon carboxylic acids include: phenylacetic, phenylpropionic, and β-benzoylaminoisobutyric acids.

Heteroarylhydrocarbon carboxylic acids for $R^6$ refers to hydrocarbon carboxylic acids substituted with an aryl group (e.g., heteroarylalkanoic acids). Examples of heteroarylhydrocarbon carboxylic acids include: 2-furanacetic acid and 3-furanpropionic acid.

The lower alkylidene groups of the alkylidenedioxy of the $R^3$ substituent represent hydrocarbon radicals having 1 to 13 carbon atoms. Examples of lower alkylidene groups include methylene, ethylidene, n-propylidene, isopropylidene, n-butylidene, and sec-butylidene.

Preferably, $R^3$ represents H, lower alkyl, or α—$OR^7$. More preferably, $R^3$ is a lower alkyl group, and most preferably $R^3$ is methyl. For example $R^3$ can be α-methyl or β-methyl, with β-methyl being preferred. The hydrocarbon carboxylic acids for $R^7$ are as defined for the hydrocarbon carboxylic acids of $R^6$.

Preferably, $R^4$ and $R^5$ are both hydrogen.

The compounds produced by the claimed process can be further reacted with reagents by processes known in the art to produce a variety of 9α-chloro-11β-hydroxypregna-3,20-diones. For example, the compound of Formula 3.0:

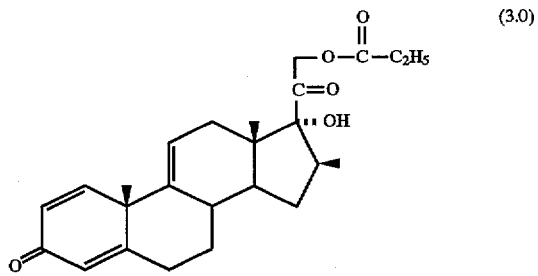

can be reacted with 1,3,5-trichloroisocyanuric acid, $CH_3SO_3H$ (methanesulfonic acid) and DMF according to the process of the invention to produce a compound of Formula 4.0:

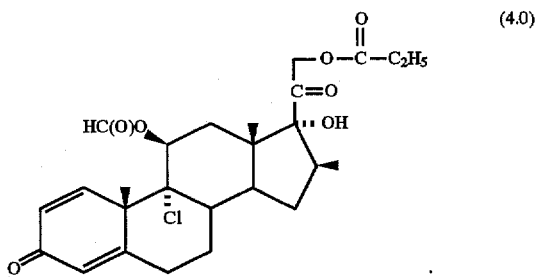

Using known techniques, Compound 4.0 can then be reacted with $(C_2H_5CO)_2O$ and 5-sulfosalicyclic acid to produce a compound of Formula 5.0:

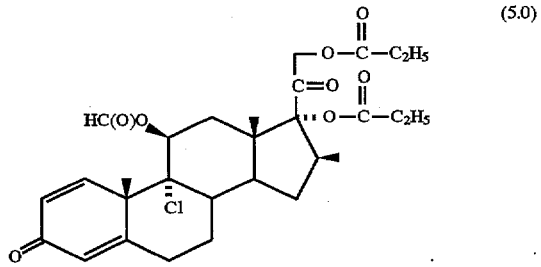

Again, using known techniques, the compound of Formula 5.0 can be reacted with a mixture of $NH_4OH$, methanol and water to hydrolyze the 11β-formyloxy group to produce the 11β-hydroxy compound of Formula 6.0:

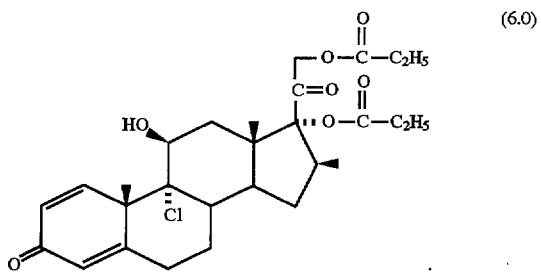

(6.0)

In an alternative reaction scheme, the compound of Formula 7.0:

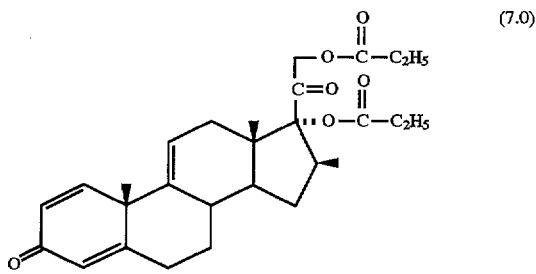

(7.0)

can be reacted with 1,3,5-trichloroisocyanuric acid, $CH_3SO_3H$ (methanesulfonic acid) and DMF according to the process of the invention to produce a compound of Formula 5.0. The compound of Formula 5.0 can then be hydrolyzed, as described above, to produce the compound of Formula 6.0.

Compounds of Formulas 3.0 and 7.0 can be produced by techniques well known in the art. The compound of Formula 6.0 is known in the art as beclomethasone dipropionate.

The examples that follow are intended to exemplify the claimed invention, and such examples should not be construed as limiting the disclosure or the claimed invention.

EXAMPLE 1

17α,21-Dihydroxy-16β-methylpregna-1,4,9($^{11}$)-triene-3,20-dione-17,21-dipropionate (Formula 7.0, 0.468 g, 1.0 mmole) and dry dimethylformamide (3 ml) was added to a dry flask. The solution was blanketed with nitrogen and cooled to about 0° C. with an ice bath. Methanesulfonic acid (0.065 ml, 1.0 mmole was added dropwise with stirring followed by 1,3,5-trichloroisocyanuric acid (0.096 g, 0.4 mmole) in portions over a time period of 15 minutes. The reaction mixture was stirred overnight at about 0° C. The reaction mixture was diluted with water after 25 hours, and then extracted with methylene chloride. The extracts were washed with brine, dried over sodium sulfate and concentrated to obtain the crude product (Formula 5.0).

Samples were taken from the above reaction and analyzed by HPLC after 2, 4, 5, 23, and 25 hours. For the HPLC analysis the solvent used was acetonitrile/water in a 60:40 ratio, the flow rate was 1.5 ml/minute, the column was a Waters μ Bondapak $C_{18}$, and detection was by UV @ 254 nm. The data given in Table 1 is area %. The dashed lines (-----) in the Table means that the peak height was insufficient for integration. The 9α-chloro, 11β-methanesulfonate by-product was isolated from the reaction mixture and identified by NMR. The 9α, 11β-dichloro by-product was identified by comparison with a standard.

TABLE 1

| Time (hours) | 9α-Cl,11β-formate (Formula 5.0) | 9α-Cl,11β-methanesulfonate (by-product) | 9α,11β-dichloro (by-product) |
|---|---|---|---|
| 2 | 70.7 | 29.0 | — |
| 4 | 71.2 | 28.5 | — |
| 5 | 71.2 | 28.6 | — |
| 23 | 70.8 | 28.6 | — |
| 25 | 71.5 | 28.0 | — |

The 9α-chloro, 11β-methanesulfonate by-product is similar in structure to the compound of Formula 5.0 with the difference being a 11β-$CH_3SO_3$- group instead of a 11β-formate group. The 9α, 11β-dichloro by-product is similar in structure to the compound of Formula 5.0 with the difference being a 11β-Cl substituent instead of a 11β-formate group.

EXAMPLE 2

Another experiment was conducted following procedures similar to those described for Example 1. In this experiment, samples were taken from the reaction mixture at 2 and 5 hours, and analyzed by HPLC. HPLC conditions similar to those described in Example 1 were used and the data obtained, as area %, is given in Table 2. The dashed lines (-----) in the Table means that the peak height was insufficient for integration.

TABLE 2

| Time (hours) | 9α-Cl,11β-formate (Formula 5.0) | 9α-Cl,11β-methanesulfonate (by-product) | 9α,11β-dichloro (by-product) |
|---|---|---|---|
| 2 | 70.0 | 29.4 | — |
| 5 | 71.4 | 28.6 | — |

The reaction mixture was then diluted with water and extracted with methylene chloride. The extracts were washed with brine, dried over sodium sulfate and concentrated to obtain the crude product. The crude product was combined with the crude product from Example 1, and the total yield of concentrated material was 1.29 g. A portion of this crude product was separated on silica gel plates of 1000 micron thickness by developing with a mixture of 9:1 methylene chloride:ethyl acetate. Under UV light of 254 nm, two major bands appeared. The more polar band had a $R_f$ of 0.35 to 0.48. The less polar band had a $R_f$ of 0.5 to 0.60.

Upon extraction from the silica gel, the Mass Spectroscopy (MS) and NMR of the more polar band (Formula 5.0) were:

(1) MS: MH$^+$549.1 (Abundance=3) and (M+2)H$^+$551.1 (Abundance=1); and (2) NMR: (DMSO) δ8.49 (1H, s), 6.90 (1H, d), 6.33 (1H, d), 6.09 (1H, s), 5.57 (1H, s), 4.74 (1H, d), and 4.41 (1H, d).

Upon extraction from the silica gel, the Mass Spectroscopy (MS) and NMR of the less polar band were:

(1) MS: MH$^+$599.5, (M+1)H$^+$600.6 and (M+2)H$^+$601.5 (Relative Abundance 100/35/43); Theory: C=58.137%, H=6.561%, S=5.351% and Cl=5.917%; Found: C=58.10%, H=6.63%, S=5.28% and Cl=not analyzed; and (2) NMR: (CDCl$_3$) δ7.32 (1H, d), 6.44 (1H, d), 6.27 (1H, s), 5.50 (1H, s), 4.90 (1H, d), 4.29 (1H, d) and 3.33 (3H, s). The less polar band was determined to be the 9α-chloro-11β-methanesulfonate by-product.

EXAMPLE 3

17α,21-Dihydroxy-16α-methylpregna-1,4,9(11)-triene-3,20-dione-21-acetate (compound of Formula 8.0)

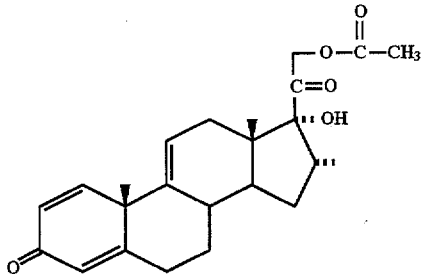

(0.398 g, 1mmole) was dissolved in 3 ml of dry dimethylformamide in a dry flask. The solution was stirred under a nitrogen atmosphere and cooled to about 0° C. with an ice bath. Methanesulfonic acid (0.065 ml, 1.0 mmole) was then added dropwise with stirring. 1,3,5-Trichloroisocyanuric acid (0.081 g, 1.017 mmole) was added in portions over a time period of about 20 minutes, and the reaction mixture was stirred at about 0° C. for about 6 hours. Then the reaction mixture was diluted with water and extracted with methylene chloride. The extracts were washed with brine, and concentrated with azeotropic drying to obtain the crude product of Formula 9.0:

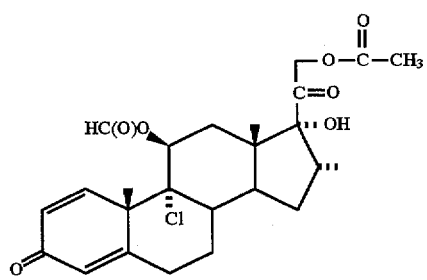

Samples were taken from the above reaction after 4.5 and 6 hours. The samples were each precipitated into water, extracted with methylene chloride, concentrated to dryness, and analyzed by HPLC. For the analysis, the solvent ratio was 65:35 methanol:water, the flow rate was 1.5 ml per minute, the column was Supelcosil LC-8, and detection was by UV at 254 nm. The results are given as area % in Table 3.

The compounds of Formulas 10.0, 11.0 and 12.0 are:

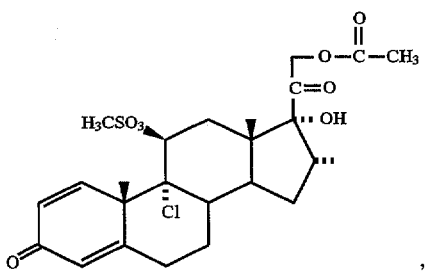

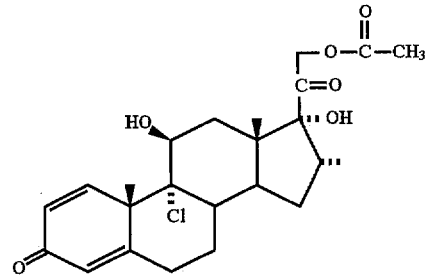

and

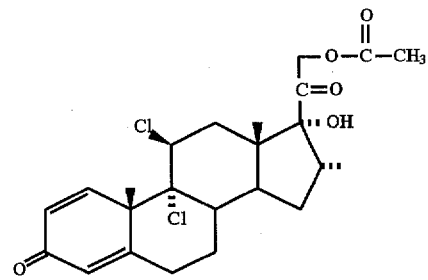

TABLE 3

| Time (hours) | Formula 9.0 | Formula 10.0 | Formula 11.0 | Formula 8.0 | Formula 12.0 |
|---|---|---|---|---|---|
| 4.5 | 60.27 | 31.70 | 0.50 | 5.98 | 0.82 |
| 6 | 73.40 | 21.88 | 0.50 | 3.26 | 0.59 |

A portion of the crude product was separated on silica gel plates of 1000 micron thickness by developing with a mixture of 85:15 methylene chloride:ethyl acetate. This development was repeated a second time to ensure complete separation of the materials. Under UV light of 254 nm, two major bands appeared. The more polar band had a $R_f$ of 0.32 to 0.46. The less polar band had a $R_f$ of 0.47 to 0.56.

Upon extraction from the silica gel, the Mass Spectroscopy (MS) and NMR of the more polar band (Formula 9.0) were:

(1) MS: MH+479 and (M+2)H+481 (Relative Abundance 100/47); and (2) NMR: (DMSO) δ8.37 (1H, s), 6.79 (1H, d), 6.24 (1H, d), 6.00 (1H, s), 5.43 (1H, s), 5.37 (1H, s), 4.91 (1H, d) and 4.73 (1H, d).

Upon extraction from the silica gel, the Mass Spectroscopy (MS) and NMR of the less polar band (Formula 10.0) were:

(1) MS: MH+529, (M+1)H+530 and (M+2)H+531 (Relative Abundance 100/28/42); and (2) NMR: (CDCl3) δ7.22 (1H, d), 6.38 (1H, d), 6.08 (1H, s), 5.40 (1H, s), 4.95 (1H, d), 4.69 (1H, d) and 3.21 (3H, s).

In this example, and in Example 4 below, compounds of Formulas 11.0 and 12.0 (impurities) were identified by comparing their HPLC retention times with the HPLC retention times of compounds whose structures were independently synthesized and whose structures were confirmed by MS and NMR. The data are:

(A) Compound of Formula 11.0:

(1) MS: MH+451 and (M+2)H+453 (Relative Abundance 100/38); and (2) NMR: (DMSO) δ7.31 (1H, d), 6.24 (1H, d), 5.99 (1H, s), 5.60 (1H, s), 5.22 (1H, s), 5.04 (1H, d), 4.80 (1H, d) and 4.26 (1H, wide singlet); and (B) Compound of Formula 12.0:

(1) MS: MH+469 and (M+2)H⁺471 (Relative Abundance 100/68); and (2) NMR: (DMSO) δ7.20 (1H, d), 6.21 (1H, d), 5.93 (1H, s), 4.93 (1H, narrow multiplet) and 4.76 (1H, d).

EXAMPLE 4

In a procedure similar to that of Example 3, except as described below, 17α,21-dihydroxy-16α-methylpregna-1,4,9($^{11}$)-triene-3,20-dione-21-acetate (Formula 8.0, 0.398 g, 1.0 mmole) and dry dimethylformamide (3 ml) were added to a dry flask. The solution was blanketed with nitrogen and cooled to about 0° C. with an ice bath. Methanesulfonic acid (0.065 ml, 1.0 mmole) was added dropwise with stirring. The solution was then cooled to about −55° C. to about −58° C. 1,3,5-Trichloroisocyanuric acid (0.086 g, 0.358 mmole) was added in portions over a time period of about 25 minutes. The reaction mixture was stirred for about 27 hours, and then 5 ml of water was added slowly to precipitate the product. The mixture was stirred well, then filtered, washed with water and dried to give the crude product of Formula 9.0 in a yield of 0.476 g.

Samples were taken from the above reaction mixture after 25 and 27 hours. The samples were precipitated into water, extracted with methylene chloride, concentrated to dryness and analyzed by HPLC. The HPLC conditions were similar to those in Example 3. The results are given as area % in Table 4. The dashed lines (------) in the Table means that the peak height was insufficient for integration.

TABLE 4

| Time (hours) | Formula 9.0 | Formula 10.0 | Formula 11.0 | Formula 8.0 | Formula 12.0 |
| --- | --- | --- | --- | --- | --- |
| 25 | 81.98 | 13.84 | 1.04 | 0.55 | — |
| 27 | 82.77 | 15.50 | 1.01 | 0.09 | 0.23 |

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A process for producing a compound of the formula:

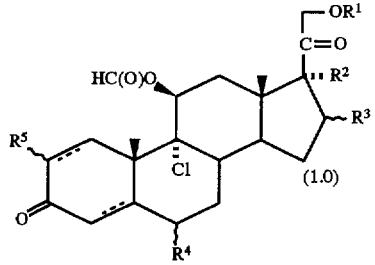

wherein:

the broken lines represent optional bonds;

R¹ represents a acyl radical of: (1) a hydrocarbon carboxylic acid having 2 to 12 carbon atoms; or (2) benzoic acid substituted by a halogen or methoxy group;

R² is selected from hydroxy or —OR⁶;

R³ is selected from hydrogen, lower alkyl, or α—OR⁷; or R² and R³ taken together represent a 16α, 17α-lower alkylidenedioxy having up to 13 carbon atoms;

R⁴ is selected from hydrogen, α-methyl, α-bromo, α-chloro, α-fluoro, β-fluoro and αfluoromethyl;

R⁵ is selected from hydrogen, methyl, fluorine, chlorine and bromine;

R⁶ is an acyl radical of: (1) a hydrocarbon carboxylic acid having from 2 to 12 carbon atoms; (2) an aromatic carboxylic acid wherein said aromatic group contains from 6 to 12 carbon atoms; (3) an arylhydrocarbon carboxylic acid wherein said aryl group contains from 6 to 12 carbon atoms, and said hydrocarbon carboxylic acid group represents a straight or branched chain carboxylic acid having from 2 to 12 carbon atoms; (4) a heteroaromatic carboxylic acid having at least one oxygen atom in the heteroaryl ring and wherein oxygen is the only heteroatom in the heteroaryl ring, and wherein the aromatic heterocyclic group contains from 2 to 14 carbon atoms; or (5) a heteroaryl-hydrocarbon carboxylic acid having at least one oxygen atom in the heteroaryl ring and wherein oxygen is the only heteroatom in the heteroaryl ring, and wherein the aromatic heterocyclic group contains from 2 to 14 carbon atoms, and said hydrocarbon carboxylic acid group represents a straight or branched chain carboxylic acid having from 2 to 12 carbon atoms; said acyl radical having from 2 to 12 carbon atoms; and R⁷ is an acyl radical of a hydrocarbon carboxylic acid having from 2 to 12 carbon atoms;

said process comprising reacting, under anhydrous conditions and under an inert atmosphere, a compound of the formula:

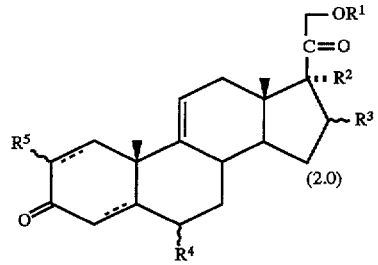

wherein R¹, R², R³, R⁴, and R⁵ are as defined above, with:

(1) a chlorinating reagent selected from an N-chloroimide or an N-chloroamide; (2) an anhydrous strong acid selected from orthophosphoric acid, alkylsulfonic acids, fluoroalkylsulfonic acids or arylsulfonic acids; and (3) anhydrous dimethyl formamide; said reaction being conducted at a temperature within the range of about −78° to about 0° C.

2. The process of claim 1 wherein said chlorinating reagent is selected from N-chloroacetamide; N-chlorosuccinimide; 1,3-dichloro-5,5-dimethyhydantoin; or 1,3,5-trichloroisocyanuric acid.

3. The process of claim 2 wherein said chlorinating reagent is selected from 1,3-dichloro-5,5-dimethylhydantoin or 1,3,5-trichloroiso-cyanuric acid.

4. The process of claim 3 wherein said chlorinating reagent is 1,3,5-trichloroisocyanuric acid.

5. The process of claim 1 wherein said acid is an alkylsulfonic acid.

6. The process of claim 5 wherein said acid is methanesulfonic acid.

7. The process of claim 1 wherein said temperature is within the range of about −55° C. to about −20° C.

8. The process of claim 1 wherein both of said optional double bonds are present.

9. The process of claim 1 wherein $R^1$ represents an acyl radical of a hydrocarbon carboxylic acid, and $R^2$ is selected from hydroxy or —$OR^6$ wherein $R^6$ is an acyl radical of a hydrocarbon carboxylic acid.

10. The process of claim 9 wherein $R^1$ is

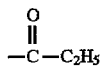

and $R^2$ is selected from hydroxy or

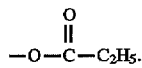

11. The process of claim 1 wherein $R^3$ is selected from H, α—$OR^7$ or a lower alkyl.

12. The process of claim 11 wherein $R^3$ is lower alkyl.

13. The process of claim 12 wherein $R^3$ is methyl, and $R^4$ and R5 are hydrogen.

14. The process of claim 1 wherein said chlorinating reagent is selected from 1,3-dichloro-5,5-dimethylhydantoin or 1,3,5-trichloroisocyanuric acid; said acid is an alkylsulfonic acid; said temperature is within the range of about −55° to about −20° C.; both optional bonds are present; $R^1$ represents an acyl radical of a hydrocarbon carboxylic acid; $R^2$ is selected from hydroxy or —$OR^6$ wherein $R^6$ is an acyl radical of a hydrocarbon carboxylic acid; and $R^3$ is selected from H, α—$OR^7$ or a lower alkyl.

15. The process of claim 14 wherein said inert atmosphere is nitrogen.

16. The process of claim 14 wherein said chlorinating reagent is 1,3,5-trichloroisocyanuric acid, and said alkylsulfonic acid is methanesulfonic acid.

17. The process of claim 16 wherein $R^1$ is

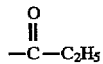

and $R^2$ is selected from hydroxy or

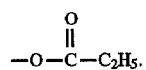

18. The process of claim 17 wherein $R^3$ is lower alkyl.
19. The process of claim 18 wherein $R^3$ is methyl.
20. The process of claim 19 wherein $R^2$ is

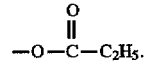

21. The process of claim 1 wherein said compound of formula 2.0 is a compound of formula 7.0:

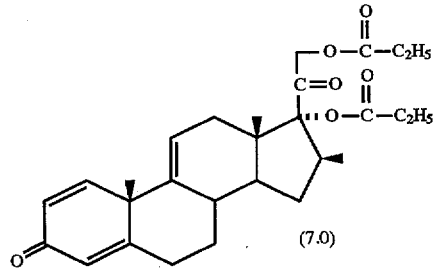

and said compound of formula 1.0 is a compound of formula 5.0:

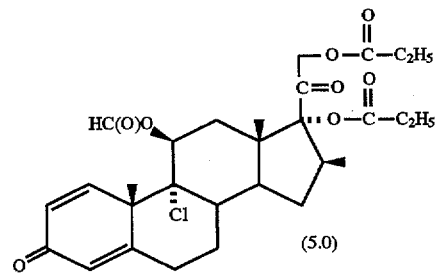

22. The process of claim 1 wherein said inert atmosphere is nitrogen.